United States Patent [19]

Ojima et al.

[11] Patent Number: 5,338,725
[45] Date of Patent: Aug. 16, 1994

[54] ANTI-AGGREGATORY AGENTS FOR PLATELETS

[75] Inventors: Iwao Ojima, Stony Brook; Masakatsu Eguchi, Setauket, both of N.Y.; Young-Im Oh, Annandale, N.J.; Barry S. Coller, Dix Hills, N.Y.

[73] Assignee: The Research Foundation of the State University of New York, Albany, N.Y.

[21] Appl. No.: 906,525

[22] Filed: Jun. 30, 1992

[51] Int. Cl.$^5$ .................. A61K 37/02; C07K 7/06; C07K 7/08
[52] U.S. Cl. .................................. 514/13; 514/14; 514/15; 514/16; 530/326; 530/327; 530/328
[58] Field of Search ........................ 514/13–16; 530/326, 327, 328

[56] References Cited

U.S. PATENT DOCUMENTS

| | | |
|---|---|---|
| 4,578,079 | 3/1986 | Ruoslahti et al. |
| 4,614,517 | 9/1986 | Ruoslahti et al. ............. 530/330 |
| 4,683,291 | 7/1987 | Zimmerman et al. ........... 530/324 |
| 4,792,525 | 12/1988 | Ruoslahti et al. ............. 530/324 |
| 4,879,313 | 11/1989 | Tjoeng et al. ................ 530/331 |
| 4,943,562 | 7/1990 | Jolles et al. . |
| 4,952,562 | 8/1990 | Klein et al. ................... 514/18 |
| 4,992,463 | 2/1991 | Tjoeng et al. ................. 514/438 |
| 5,023,233 | 6/1991 | Nutt et al. .................... 514/11 |
| 5,041,380 | 8/1991 | Ruoslahti et al. ............. 530/330 |
| 5,051,405 | 9/1991 | Klein et al. ................... 514/18 |
| 5,053,392 | 10/1991 | Klein et al. ................... 514/18 |
| 5,053,393 | 10/1991 | Tjoeng et al. ................. 514/18 |

FOREIGN PATENT DOCUMENTS

| | | |
|---|---|---|
| 0220957A2 | 5/1987 | European Pat. Off. . |
| 0341915A2 | 11/1989 | European Pat. Off. . |
| 0352249A1 | 1/1990 | European Pat. Off. . |
| 0410537A1 | 1/1991 | European Pat. Off. . |
| 0411833A1 | 2/1991 | European Pat. Off. . |
| 0422937A1 | 4/1991 | European Pat. Off. . |
| 0425212A2 | 5/1991 | European Pat. Off. . |
| WO89/07609 | 8/1989 | PCT Int'l Appl. . |

OTHER PUBLICATIONS

Green et al., *Anticoagulant, Spectrum Biotechnology Applications*, Decision Resources, Inc. (Aug. 8, 1991).
Samenan et al, *J. Med. Chem.*, 34, 3114–3125 (1991).
Kawasaki et al, *Chem. Pharm. Bull.* 39(12) 3373–3375 p. (1991).

*Primary Examiner*—Merrell C. Cashion, Jr.
*Assistant Examiner*—S. G. Marshall
*Attorney, Agent, or Firm*—Hoffmann & Baron

[57] ABSTRACT

The present invention provides synthetic antiaggregatory agents for preventing inhibition of fibrinogen-platelet binding. These anti-aggregatory agents have the general formulas (1)–(5).

$$H-[-(AA_i)_i-R-G-D-(AA_j)_j-]_n-Cx \quad (1)$$

$$[R_i-C(O)-R-G-D-(AA_j)_j-]_n-CX \quad (2)$$

$$Cy-[-AA_i)_i-R-G-D-(AA_j)_i-]_n-Z \quad (3)$$

$$H-[-(AA_i)_i-R-G-D-(AA_j)_j-]_n-C-Z-[-(AA_k)_k-R-G-D-(AA_l)_l-]_m-Z \quad (4)$$

$$[R_1-C(O)-R-G-D-(AA_i)_i-]_n-CZ[-(AA_j)_j-]-R-G-D-(AA_k)_k-]_m-Z \quad (5)$$

in which: R=Arg; G=Gly; D=Asp; $AA_i$, $AA_j$, $AA_k$ and $AA_l$ = alpha-, beta- and omega-amino acid residues; $(AA_i)_i$ $(AA_j)_j$ =peptide chains having the same or different amino acid residues; $(AA_k)_k$ =peptide chains having the same or different amino acid residues; $(AA_l)_l$ =peptide chains having the same or different amino acid residues; i and j =integers 0–20; m =an integer 1–10; n=an integer 2–10; Cx =a conjugator bearing at least two amine residues in a molecule having 1–30 carbon atoms, i.e, diamines, triamines, tetramines, and polyamines, which can have other functional groups in the molecule; Cy =a conjugator bearing at least two carboxyl residues in a molecule having 1–30 carbon atoms, i.e., aliphatic, aromatic, heteroaromatic, cycloalkyl dicarboxylic acid, tricarboxylic acid, and (Abstract continued on next page.)

polycarboxylic acid residues, which can have other functional groups in the molecule; Cz =a conjugator bearing at least one amine residue and one carboxyl residue in an aromatic or a cycloalkyl skeleton, having 1–30 carbon atoms, i.e., aromatic, heteroaromatic and cycloalkyl amino carboxylic acid, diamino carboxylic acid, diamino dicarboxylic acid, and ployamino polycarboxylic acid residues; $R_1$=an alkyl, aromatic, heteroaromatic, or cycloalkyl group having 1–30 carbons, which can have other functional groups in the molecule; and Z=carboxyl, amide, N-substituted amide, hydrazide, N-substituted hydrazide, or ester group.

5 Claims, No Drawings

ANTI-AGGREGATORY AGENTS FOR PLATELETS

BACKGROUND OF THE INVENTION

1. Field of the Invention

The present invention relates to anti-aggregatory agents for platelets, specifically oligopeptides which inhibit fibrinogen-platelet binding.

2. Background of the Related Art

The control and selective prevention of uncontrolled clotting is an important medicinal and clinical goal. The production of a blood clot in response to an injury can often become life-threatening when occurring at inopportune times and locations in the circulatory system.

Human blood platelets function to prevent bleeding by adhering to the surface of damaged blood vessels and then aggregating with one another. In pathological conditions, platelet aggregation and thrombus formation can be inappropriate, leading to occlusion of blood vessels, as occurs in heart attacks and strokes. These thrombotic diseases are some of the most common cause of death each year throughout the world. In addition, this same process is responsible for venous thrombosis, pulmonary embolism, and failure of vascular graft surgery, which are all serious medical problems affecting millions of patients; See, Green et al., "Anticoagulant Biotherapeutics for Heart Disease and Stroke" *Anticoagulant, Spectrum Biotechnology Applications*, Decision Resources, Inc. (Aug. 8, 1991).

A blood clot can obstruct a vessel, stop the supply of blood to the heart, limb or to an essential organ. Clots which become detached, called embolisms can flow through the circulatory system causing blockages at sites which are remote from the point of original injury and clot. If processes for blood clotting could be controlled, sufficient clotting can be obtained to allow healing of an injury without creating uncontrolled thrombi. Control of the clotting mechanism may be useful in preventing heart attacks due to reocclusion at the site of a clot, strokes, injuries due to embolisms and other clotting related injuries.

There are three related mechanisms involved in blood coagulation. The coagulation cascade leads to the generation of thrombin resulting in the conversion of fibrinogen to fibrin, a mesh-like structure that makes up a clot. The thrombolytic mechanism leads to clot dissolution by converting plasminogen into the clot-digesting enzyme plasmin. Platelet adhesion and aggregation, the third mechanism, contribute to clot formation by forming a cellular plug and by enhancing thrombin formation. Platelets may be activated by several different agonists such as adenosine diphosphate (ADP), epinephrine, collagen and thrombin that are released in the circulatory system in response to injury. These agonists have the ability to alter the surface glycoprotein GPIIb/IIIa receptors of platelets so that they can bind fibrinogen and other adhesive glycoproteins. Fibrinogen, a dimeric molecule binds to two platelets simultaneously and acts as a bridging molecule, producing an extensive lattice formation. The GPIIb/IIIa receptors are present at a very high density on the surface of platelets, each platelet containing approximately 40,000–50,000 such receptors.

The importance of the GPIIb/IIIa receptors in platelet aggregation is demonstrated by the failure of platelets to aggregate when taken from patients suffering from Glanzmann thrombasthenia, who lack the GPIIb/IIIa receptor, and the ability of monoclonal antibodies to the GPIIb/IIIa receptor to abolish platelet aggregation. Accordingly, non-immunogenic peptide-based inhibitors with high specificities would have tremendous therapeutic potential. These type of inhibitors could offer the prospect of rapid inhibition of platelet aggregation. In addition, they could be given repeatedly since they are small enough to be non-immunogenic. This is a substantial advantage over monoclonal antibodies which may be immunogenic.

The GPIIb/IIIa receptor is part of a superfamily of adhesion receptors, many of which share a common recognition site for peptides containing the short hydrophilic amino acid sequence arginine-glycine-aspartic acid (RGD). In fact, all proteins that bind to the platelets GPIIb/IIIa receptor, for example fibrinogen, von Willebrand factor, fibronectin and vitronectin have RGD sequence in their cell binding domains. Synthetic peptides containing this sequence act as competitive, reversible inhibitors in assays of cellular adhesion. They compete directly for fibrinogen binding sites on platelets in a noncytotoxic manner.

Various linear RGD peptides have been synthesized for the purpose of preventing platelet aggregation, for example see, Samanen et. al., *J. Med. Chem.*, 34, 3114–3125 (1991). Many of those synthetic linear RGD peptides are described in U.S. Pat. Nos. 5,047,380; 4,683,291; 4,578,079; 4,614,517; 4,792,525; 4,992,463; and in European Patent Publication EP 298 820 A1. U.S. Pat. No. 4,683,291 in addition to disclosing linear RGD peptides also discloses linear RGD polypeptides and branched RGD containing peptides.

Various cyclic peptides containing the RGD sequence have also been synthesized, as described in U.S. Pat. No. 5,023,233 and in foreign patent publications EP 425 212 A2; EP 410 537 A1; JP 2-174797 and GP 3,41915 A2, and PCT publication WO 90/02751.

Therefore, a purpose of the present invention is to control the blood coagulation process by providing peptide based agents which competitively inhibit fibrinogen-platelet binding.

Another purpose of this invention is to provide oligopeptides that cannot easily be degraded by hydrolytic enzymes, i.e. proteases and peptidases, in the circulatory system, and allow these oligopeptides to inhibit fibrinogenplatelet binding.

A further purpose of the present invention is the production of peptide based agents which are non-immunogenic and highly efficient in preventing fibrinogen-platelet binding so that these agents can serve as therapeutic drugs.

SUMMARY OF THE INVENTION

These purposes and goals are satisfied by the present invention which provides synthetic anti-aggregatory agents for preventing inhibition of fibrinogen-platelet binding. These anti-aggregatory agents have the general formulas (1)–(5).

$$H-[-(AA_i)_i-R-G-D-(AA_j)_j-]_n-Cx \quad (1)$$

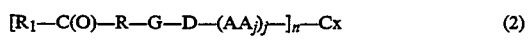

$$[R_1-C(O)-R-G-D-(AA_j)_j-]_n-Cx \quad (2)$$

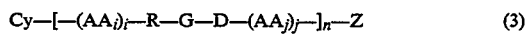

$$Cy-[-(AA_i)_i-R-G-D-(AA_j)_j-]_n-Z \quad (3)$$

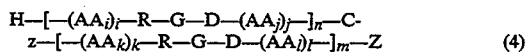

$$H-[-(AA_i)_i-R-G-D-(AA_j)_j-]_n-C-$$
$$z-[-(AA_k)_k-R-G-D-(AA_l)_l-]_m-Z \quad (4)$$

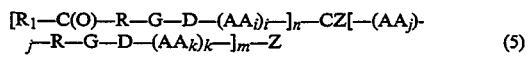

$$[R_1-C(O)-R-G-D-(AA_i)_i-]_n-CZ[-(AA_j)_j-R-G-D-(AA_k)_k-]_m-Z \quad (5)$$

in which:
R=Arg; G=Gly; D=Asp;
$AA_i$, $AA_j$, $AA_k$ and $AA_l$=alpha-, beta- and omega-amino acid residues;
$(AA_i)_i$=peptide chains having the same or different amino acid residues;
$(AA_j)_j$=peptide chains having the same or different amino acid residues;
$(AA_k)_k$=peptide chains having the same or different amino acid residues; and
$(AA_l)_l$=peptide chains having the same or different amino acid residues;
i and j=integers 0-20;
m=an integer 1-10;
n=an integer 2-10;
Cx=a conjugator bearing at least two amine residues in a molecule having 1-30 carbon atoms, i.e, diamines, triamines, tetramines, and polyamines, which can have other functional groups in the molecule;
Cy=a conjugator bearing at least two carboxyl residues in a molecule having 1-30 carbon atoms, i.e., aliphatic, aromatic, heteroaromatic cycloalkyl dicarboxylic acid, tricarboxylic acid, and polycarboxylic acid residues, which can have other functional groups in the molecule;
Cz=a conjugator bearing at least one amine residue and one carboxyl residue in an aromatic or a cycloalkyl skeleton, having 1-30 carbon atoms, i.e., aromatic, heteroaromatic and cycloalkyl amino carboxylic acid, diamino carboxylic acid, diamino dicarboxylic acid, and ployamino polycarboxylic acid residues;
$R_1$=an alkyl, aromatic, heteroaromatic, or cycloalkyl group having 1-30 carbons, which can have other functional groups in the molecule;
Z=carboxyl, amide, N-substituted amide, hydrazide, N-substituted hydrazide, or ester group.

For a better understanding of the present invention, reference is made to the following description and the accompanying tables, the scope of which is pointed out in the claims.

DETAILED DESCRIPTION OF THE INVENTION

In accordance with the preferred embodiments of the present invention, the inventors have synthesized new peptides bearing more than one RGD sequences in a branched manner to obtain better binding to the GPIIb/IIIa receptor than that shown by single RGD peptides of the prior art. Linear peptides containing non-natural protein amino acid residues or non-amino acid residues have also been synthesized to determine their effect on the inhibition of platelet aggregation.

Increasing the number of RGD sequence in a molecule which interacts with the receptor should enhance its overall inhibitory activity, i.e., higher local concentrations of the RGD sequence should provide better inhibitory activity because the probability that they would interact with the receptor should be increased. This is the concept upon which the RGD peptide based anti-aggregatory agents of the present invention were developed. In addition to naturally occurring protein amino acid residues, synthetic, non-naturally occurring protein amino acid residues as well as non-amino acid residues have been introduced to prevent degradation by proteases and peptidases in the circulatory system.

More than one, and up to a maximum of three (3) RGD units combined with a conjugator, forms the basic structure of the RDG peptide based anti-aggregatory agents of the present invention. The conjugator can be a diamino acid, a dicarboxylic acid, tricarboxylic acid, diamine and so on. Modification of the conjugator is sometimes critical to obtain high inhibitory activity because the structure of the conjugator influences the conformation of the RGD sequence. Also, the length of the conjugator is crucial. It should not be too long to avoid the promotion of platelet aggregation, which may be caused by accommodation of two platelets by two RGD units. Furthermore, when branching is increased to a much higher level, the poly-RGD peptide loses its inhibitory activity. For example, a highly branched RGD peptide, $[(GRGDF)_2K]_2K-NH_2$ that has four (4) RGD sequences does not show any inhibitory activity even at a concentration of $1\times10^{-3}$ M.

The preferred anti-aggregatory agents for inhibiting fibrinogen-platelet binding, according to the present invention have the general formula (1)-(5):

$$H-[-(AA_i)_i-R-G-D-(AA_j)_j-]_n-Cx \qquad (1)$$

preferably, $(RGDFPG)_2Dab-G-OH$ $(RGDFPG)_2Dab-NH_2$ $(RGDF)_2Lys-NH_2$ $(GRGDF)_2Lys-NH_2$ $(GRGDF)_2Orn-NH_2$ $(RGDF)_2Dac-NH_2$ $$[R_1-C(O)-R-G-D-(AA_j)_j-]_n-Cx \qquad (2)$$

preferably, $(BzRGDF)_2Lys-NH_2$ $(HexRGDF)_2Lys-NH_2$ $(BzRGDFP)_2Lys-NH_2$ $(HexRGDFP)_2Lys-NH_2$ $$Cy-[-(AA_i)_i-R-G-D-(AA_j)_j-]_n-Z \qquad (3)$$

preferably, $(p)Pht(RGDF-OH)_2$ $Suc(RGDF-OH)_2$ $Pda(RGDF-OH)_2$ $Bda(RGDF-OH)_2$ $$\begin{aligned}H-[-(AA_i)_i-R-G-D-(AA_j)_j-]_n-C\\z-[-(AA_k)_k-R-G-D-(AA_l)_l-]_m-Z\end{aligned} \qquad (4)$$

preferably, $(GRGDFG)_2Dab-GRGDF-NH_2$ $(RGDF)_2Dac-RGDF-OH$ (GRGDSG)$_2$Dab—GRGDS—OH (RGDV)$_2$Lys—GRGDV—NH$_2$ (GRGDF)$_2$Lys—GRGDF—NH$_2$ (GRGDF)$_2$Orn—GRGDF—NH$_2$ GRGDFG—(o) Abz—GRGDF—OH GRGDFG—(m) Abz—GRGDF—OH GRGDFG—(p) Abz—GRGDF—OH GRGDFG—(o) Abz—GRGDF—NH$_2$ GRGDFG—(m) Abz—GRGDF—NH$_2$ GRGDFG—(p) Abz—GRGDF—NH$_2$ GRGDSG—(o) Abz—GRGDF—NH$_2$ GRGDSG—(m) Abz—GRGDF—NH$_2$ GRGDSG—(p) Abz—GRGDF—NH$_2$ GRGDVG—(o) Abz—GRGDF—NH$_2$ GRGDVG—(m) Abz—GRGDF—NH$_2$ GRGDVG—(p) Abz—GRGDF—NH$_2$ $$R_1-C(O)-R-G-D-(AA_i)_i-]_n-CZ[-(AA_j)_j-R-G-D-(AA_k)_k-]_m-Z \quad (5)$$

preferably, (BzRGDF)$_2$Dac—RGDF—OH, in which:
R=Arg; G=Gly; D=Asp;
(AA$_i$)$_i$ =peptide chains having the same or different amino acid residues;
(AA$_j$)$_j$=peptide chains having the same or different amino acid residues;
(AA$_k$)$_k$=peptide chains having the same or different amino acid residues; and
(AA$_l$)$_l$=peptide chains having the same or different amino acid residues;
i and j =integers 0-20;
m=an integer 1-10;
n=an integer 2-10;
Cx=a conjugator bearing at least two amine residues in a molecule having 1-30 carbon atoms, i.e, diamines, triamines, tetramines, and polyamines, which can have other functional groups in the molecule;
Cy=a conjugator bearing at least two carboxyl residues in a molecule having 1-30 carbon atoms, i.e., aliphatic, aromatic, heteroaromatic, cycloalkyl dicarboxylic acid, tricarboxylic acid, and polycarboxylic acid residues, which can have other functional groups in the molecule;
Cz=a conjugator bearing at least one amine residue and one carboxyl residue in an aromatic or a cycloalkyl skeleton, having 1-30 carbon atoms, i.e., aromatic, heteroaromatic and cycloalkyl amino carboxylic acid, diamino carboxylic acid, diamino dicarboxylic acid, and ployamino polycarboxylic acid residues;

$R_1$=an alkyl, aromatic, heteroaromatic, or cycloalkyl group having 1-30 carbons, which can have other functional groups in the molecule;
Z=carboxyl, amide, N-substituted amide, hydrazide, N-substituted hydrazide or ester group.

The non-naturally occurring protein amino acid residues and non-amino acid residues include: Dab=3,5-Diaminobenzoic acid residue; Abz=Aminobenzoic acid residue; Dac=3,5-Diaminocyclohexanecarboxylic acid residue; Pht=Phthalic acid residue; Suc=Succinic acid residue; Pda =Propanedicarboxylic acid residue; Bda=Butanedicarboxylic acid residue; (o)=ortho; (m)=meta; and (p)=para.

The common naturally-occurring protein amino acids are:

| NATURAL AMINO ACIDS | | |
|---|---|---|
| Name | 3-Letter Abbreviation | 1-Letter Abbreviation |
| (+)-Alanine | Ala | A |
| (+)-Arginine | Arg | R |
| (−)-Asparagine | Asn | N |
| (+)-Aspartic acid | Asp | D |
| (−)-Cysteine | Cys | C |
| (+)-Glutamic acid | Glu | E |
| (+)-Glutamine | Gln | Q |
| Glycine | Gly | G |
| (−)-Histidine | His | H |
| (+)-Isoleucine | Ile | I |
| (−)-Leucine | Leu | L |
| (+)-Lysine | Lys | K |
| (−)-Methionine | Met | M |
| (−)-Phenylalanine | Phe | F |
| (−)-Proline | Pro | P |
| (−)-Serine | Ser | S |
| (−)-Threonine | Thr | T |
| (−)-Tryptophane | Trp | W |
| (−)-Tyrosine | Tyr | Y |
| (−)-Valine | Val | V |

Theraputic Dosage Formulations

In the management of thromboembolic disorders the compounds of this invention may be utilized in compositions such as tablets, capsules or elixers for oral administration, suppositories for rectal administration, sterile solutions or suspensions for injectable administration, and the like. Animals in need of treatment using compounds of this invention can be administered dosages that will provide optimal efficacy. The dose and method of administration will vary from animal to animal and be dependent upon such factors as weight, diet, concurrent medication and other factors which those skilled in the medical arts will recognize.

Dosage formulations of the anti-aggregatory agents of the present invention are prepared for storage or administration by mixing the anti-aggregatory agents having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspattic acid, or arginine; monosaccharides, disaccharides, and other carbohydrates including cellulose or its derivatives, glucose, mannose, or dextrins; chelating agents such as EDTA; sugar alcohols such as mannitol or sobitol; counterions such as sodium and/or nonionic surfactants such as Tween, Pluronics or polyethyleneglycol.

Dosage formulations of the anti-aggregatory agents of the present invention to be used for therapeutic administration must be sterile. Sterility is readily accomplished by filtration through sterile filtration membranes such as 0.2 micron membranes. Anti-aggregatory formulations ordinarily will be stored in lyophilized form or as an aqueous solution. The pH of the anti-aggregatory preparations typically will be between 3 and 11, more preferably from 5 to 9 and most preferably 7 and 8. It will be understood that use of certain of the foregoing excipients, carriers, or stabilizers will result in the formation of salts of the anti-aggregatory peptides. While the preferred route of administration is by hypodermic injection needle, other methods of administration are also anticipated such as suppositories, aerosols, oral dosage formulations and topical formulations such as ointments, drops and dermal patches.

Therapeutic anti-aggregatory formulations generally are placed into a container having a sterile access port, for example, an intravenous solution bag or vial having a stopper pierceable by hypodermic injection needle.

Therapeutically effective dosages may be determined by either in vitro or in vivo methods. One method of evaluating therapeutically effective dosages is the in vitro platelet aggregation inhibitory assay described below. Based upon such in vitro assay techniques, a therapeutically effective dosage range may be determined. For each particular anti-aggregatory peptide formulation of the present invention, individual determinations may be made to ascertain the optimal dosage required. The range of therapeutically effective dosages will naturally be influenced by the route of administration. For injection by hypodermic needle it may be assumed the dosage is delivered into the body's fluid. For other routes of administration, the absorption efficiency must be individually determined for each anti-aggregatory peptide formulation by methods well known in pharmacology.

The range of therapeutic dosages may range from about 0.01 nM to about 1.0 mM, more preferably from 0.1 nM to about 100 $\mu$M, and most preferably from about 1.0 nM to 50 $\mu$M.

A typical formulation of compounds of Formulae (1)–(5) as pharmaceutical compositions contain from about 0.5 to 500 mg of a compound or mixture of compounds as either the free acid or base form or as a pharmaceutically acceptable salt. These compounds or mixtures are then compounded with a physiologically acceptable vehicle, carrier, excipient, binder, preservative, stabilzer, or flavor, etc., as called for by accepted pharmaceutical practice. The amount of active ingredient in these compositions is such that a suitable dosage in the range indicated is obtained.

Typical adjuvants which may incorporated into tablets, capsules and the like are a binder such as acacia, corn starch or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixer may contain the active compound, a sweetener such as sucrose, preservatives like propylparaben, a coloring agent and a flavoring agent such as cherry. Sterile compositions for injection can be formulated according to conventional pharmaceutical practice. For example, dissolution or suspension of the active compound in a vehicle such as water or naturally occuring vegatable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Experimental Procedures

1. In vitro Inhibition of Aggregation of Human Platelet-Rich Plasma

Whole blood (10 ml) was collected from human volunteers and anticoagulated by addition of 100 ml of 40% sodium citrate. Platelet-rich plasma (PRP) was prepared by low speed centrifugation (700 G for 3.5 min at 22° C.). The PRP was removed and the remaining blood was centrifuged at 2000 G for 10 min at 22 ° C. to obtain platelet poor plasma (PPP). The PRP was diluted with PPP to give a final platelet count of 300 000$\mu$L with a Coulter Acounter Model ZM (Coulter, Hialeah, Fla.). This diluted PRP (400$\mu$L) was placed in a siliconized glass cuvette equipped with a magnetic stirrer and stirred at 1200 rpm at 37° C. Various concentrations of the peptides (36$\mu$L) in TRIS buffer (0.01 M TRIS, 0.15 M NaCl, and 0.05% sodium azide, pH 7.4) was added and incubated for 3 rain before platelet aggregation was induced by addition of 54$\mu$L of 100$\mu$M ADP in HEPES buffer ( 0.01 M HEPES and 0.15 M NaCl, pH 7.5). The platelet aggregation was determined by a change in light transmission through the PRP on a Lumi Aggregometer 400rS (ChronoLog, Hayertown, PA). The ability of the peptides to inhibit platelet aggregation was evaluated and the $IC_{50}$ was determined as the concentration of peptide required to produce 50% inhibition of the response to ADP in the presence of the TRIS buffer.

2. Comparison of Different Assay Methods

The assay system developed by Coller, which is used throughout the experiment, is different from conventional assay systems in certain aspects. First, the platelets used by Plow et al., *Blood,* 70, 110 (1987); and Garsky et al., *Proc. Natl. Acad. Sci. U.S.A.,* 86, 4022 (1989) are gel-filtered to remove plasma proteins. Since the gel-filtration treatment may decrease the reactivity of the platelets, our assay avoids this step. The platelet count is adjusted by simply mixing PRP and PPP, which minimizes alterations of the platelets. Second, fibrinogen concentration in the Coller system is different from that of others. As shown in the experimental description of the assay, PRP was obtained from fresh blood and used immediately without further manipulation except for count adjustment. According to measurements obtained using this assay, such plasma contains ca. 3 mg of fibrinogen per 1 mL of plasma. On the other hand, fibrinogen concentration used in the Garsky and Plow assay system is 0.1 mg/mL. The concentration of fibrinogen affects the amount of RGD peptide required to inhibit platelet aggregation, with higher fibrinogen concentrations resulting in higher $IC_{50}$ values. If there is a linear relationship between these two parameters, the $IC_{50}$ values obtained from the Coller assay should be ca. 30 times larger than those obtained from the Plow et al. assay or the Garsky et al. assay. The adjusted $IC_{50}$ values are presented in column 4 of Table showing the inhibitory activities of RGD peptides.

3. Materials for the Synthesis of Peptides

N-9-Fluorenylmethoxycarbonylamino acids (Fmoc amino acids) were purchased from E. I. du Pont de Nemours & Co.(Boston, Mass.), Sigma Chemical Co.(St. Louis, Miss.), Peptides International Inc.(Louisville, Ken.), and AminoTech Inc. RAPID AMIDE TM resin and WANG TM resin were purchased from E. I. du Pont de Nemours & Co. All solvents were purchased from Aldrich Chemical Co. (Milwaukee, Wis.), J. T. Baker Inc. (Phillipsburg, N.J.) and, Fisher Scientific Co.(Pittsburgh, Pa.) 1-Hydroxybenzotriazole (HOBt), thioanisol, 1,2-ethanedithiol, and diisopropylcarbodiimide (DIC) were purchased from E. I. du Pont de Nemours & Co. Liquified phenol was purchased from Fisher Scientific Co. All other reagents were purchased from Aldrich Chemical Co.(Milwaukee, Wis.).

4. General Procedure for the Synthesis of Peptides

Solid phase peptide synthesis was carried out on a Du Pont RAMPS ® Multiple Peptide Synthesis System. High performance liquid chromatography (HPLC, preparative and analytical) was carried out by using a Waters µBondaPak C-18 column on a HPLC assembly consisting of a Waters 600E Multisolvent Delivery System, a Waters 484 tunable absorbance detector and a NEC Powermate workstation a with Microsoft Baseline 810 program (Waters, Milford, Mass.).

A cycle of the peptide coupling procedure included one of the following operations:

(A) The procedure for peptides having an amide terminus (the entire procedure was operated at ambient temperature). The RAPID AMIDE TM resin (0.1 mmol) was prepared for coupling by neutralization using 50% piperidine in dimethylformamide (DMF) (2 mL). The resin was washed with DMF (3×2 mL), methanol (3×2 mL) and again with DMF (4×2 mL). The Fmoc amino acid was then activated via the pentafluorophenyl (Pfp) ester (vide infra) or HOBt ester (vide infra) methods followed by addition of the activated Fmoc amino acid to the RAPID AMIDE TM resin. The resulting mixture was rocked for 2 h periods for coupling reaction. Coupling was followed by rinsing with DMF (3×2 mL), MeOH (3×2 mL), then with DMF (4×2 mL). The Fmoc group of the last coupled amino acid was removed using 50% piperidine in DMF (2 mL). The resin was washed alternately with DMF (3×2 mL) and methanol (3×2 mL) and again with DMF (4×2 mL) for the next coupling process. When the last amino acid had been coupled, the peptide was cleaved from the resin using TFA (2.85 mL), liquified phenol (185 µL), and 1,2-ethanedithiol (15 µL). The peptide thus obtained was washed with ether (4×20 mL), dissolved in water (1 mL) and lyophilized to give a white solid. All peptides were purified by preparative reversed-phase HPLC using a Waters µBondaPak C-18 (19 mm×15 cm) column.

(B) The procedure for peptides having a carboxyl acid terminus (the entire procedure was operated at ambient temperature). The WANG TM resin (0.1 mmol) was prepared for coupling by the deprotection of Fmoc group of the amino acid which was already attached to the resin using 50% piperidine in DMF (2 mL) and washing with DMF (3×2 mL), methanol (3×2 mL) and again with DMF (4×2 mL). The Fmoc amino acid was then activated via the pentafluorophenyl (Pfp) ester (vide infra) or HOBt ester (vide infra) methods followed by addition of the activated Fmoc amino acid to the WANG TM resin. The resulting mixture was rocked for 2 h periods for coupling reaction. Coupling was followed by rinsing with DMF (3×2 mL), MeOH (3×2 mL), then with DMF (4×2 mL). The Fmoc group of the last coupled amino acid was removed using 50% piperidine in DMF (2 mL). The resin was washed alternately with DMF (3×2 mL) and methanol (3×2 mL) and again with DMF (4×2 mL) for the next coupling process. When the last amino acid had been coupled, the peptide was cleaved from the resin using TFA (2.85 mL), thioanisol (185 µL), and 1,2-ethanedithiol (15 µL). The peptide thus obtained was washed with ether (4×20 mL), dissolved in water (1 mL) and lyophilized to give a white solid. All peptides were purified by preparative reversed-phase HPLC using a Waters µBondaPak C-18 (19 mm×15 cm) column.

5. Activation of Fmoc-amino acids by Pfp ester method

A suspension of the Fmoc-amino acid (0.25 mmol) in dichloromethane (1 mL) was stirred at 0 ° C. for 5 min. To this suspension was added pentafluorophenol (0.25 retool) in DMF (46 mL of a 5.4 M solution) and DIC (39 mL) at 0 ° C. The mixture was stirred for 5 rain at room temperature. A solution of HOBt in DMF (0.2 mL of a 0.5 M solution) was added directly to the resin, followed by the activated amino acid solution. The vial was rinsed with DMF (2 mL) and the washings were added to the resin.

6. Activation of Fmoc-amino acids by HOBt ester method

A suspension of the Fmoc-amino acid (0.25 mmol) in dichloromethane (1 mL) was stirred at 0° C. for 5 min. To this suspension was added HOBt (0.5 mL of a 0.5 M solution) and DIC (39 mL) at 0° C. The mixture was stirred for 5 rain at room temperature. The activated amino acid solution was added directly to the resin. The vial was rinsed with DMF (2 mL) and the washings were added to the resin.

7. Amino Acid Analysis of Peptides

The analyses were carried out through the Waters PICO.TAG TM procedure. The peptides were hydrolyzed with PICO.TAG TM 1% liquified phenol in 6 N HCl at 100 ° C. for 24 hours. The resulting mixture of amino acids were derivatized with 20 mL of phenyl isothiocyanate. The derivatized amino acids were analyzed on a Waters PICO.TAG TM column by using a gradient of 6% acetonitrile (triethylamine-sodium acetateacetic acid buffer pH 6.4) to 30% acetonitrile over a period of 10 min at a flow rate of 1.0 mL/min.

The following peptides were synthesized, and their amino acid contents were analyzed as described in procedures 3–7, above. In addition, their ability to inhibit aggregation of human platelet rich plasma was assessed as described in procedures 1 and 2, above. Their respective $IC_{50}$ values, as well as their estimated $IC_{50}$ adjusted to the values according the method of Plow et al., (vide supra) are listed in Table 1.

TABLE 1

| Example | Peptide | Formula (1)–(5) | IC$_{50}$ (M) | IC$_{50}$ (M)* |
|---|---|---|---|---|
| 1 | (RGDFPG)$_2$Dab—G—OH | 1 | $2.0 \times 10^{-5}$ | $6.7 \times 10^{-7}$ |
| 2 | (RGDFPG)$_2$Dab—NH$_2$ | " | $1.3 \times 10^{-5}$ | $4.2 \times 10^{-7}$ |
| 3 | (RGDF)$_2$Lys—NH$_2$ | " | $3.5 \times 10^{-5}$ | $1.2 \times 10^{-6}$ |
| 4 | (GRGDF)$_2$Lys—NH$_2$ | " | $1.1 \times 10^{-4}$ | $3.5 \times 10^{-6}$ |
| 5 | (GRGDF)$_2$Orn—NH$_2$ | " | $1.3 \times 10^{-4}$ | $4.4 \times 10^{-6}$ |
| 6 | (RGDF)$_2$Dac—NH$_2$ | " | $5.0 \times 10^{-5}$ | $1.7 \times 10^{-6}$ |
| 7 | (BzRGDF)$_2$Lys—NH$_2$ | 2 | $8.8 \times 10^{-6}$ | $2.9 \times 10^{-7}$ |
| 8 | (HexRGDF)$_2$Lys—NH$_2$ | " | $2.3 \times 10^{-6}$ | $7.6 \times 10^{-8}$ |
| 9 | (BzRGDFP)$_2$Lys—NH$_2$ | " | $3.7 \times 10^{-6}$ | $1.2 \times 10^{-7}$ |
| 10 | (HexRGDFP)$_2$Lys—NH$_2$ | " | $2.7 \times 10^{-6}$ | $9.0 \times 10^{-8}$ |
| 11 | (p)Pht(RGDF—OH)$_2$ | 3 | $1.3 \times 10^{-5}$ | $4.2 \times 10^{-7}$ |
| 12 | Suc(RGDF—OH)$_2$ | " | $1.5 \times 10^{-5}$ | $5.0 \times 10^{-7}$ |
| 13 | Pda(RGDF—OH)$_2$ | " | $1.5 \times 10^{-5}$ | $5.0 \times 10^{-7}$ |
| 14 | Bda(RGDF—OH)$_2$ | " | $1.4 \times 10^{-5}$ | $4.7 \times 10^{-7}$ |
| 15 | (GRGDFG)$_2$Dab—GRGDF—NH$_2$ | 4 | $3.3 \times 10^{-5}$ | $1.1 \times 10^{-6}$ |
| 16 | (GRGDFG)$_2$Dac—RGDF—OH | " | $2.2 \times 10^{-5}$ | $7.2 \times 10^{-7}$ |
| 17 | (GRGDFG)$_2$Lys—GRGDF—NH$_2$ | " | $5.1 \times 10^{-5}$ | $1.7 \times 10^{-6}$ |
| 18 | (GRGDFG)$_2$Orn—GRGDF—NH$_2$ | " | $6.2 \times 10^{-5}$ | $2.1 \times 10^{-6}$ |
| 19 | GRGDFG-(o)Abz—GRGDF—OH | " | $6.3 \times 10^{-5}$ | $2.1 \times 10^{-6}$ |
| 20 | GRGDFG-(m)Abz—GRGDF—OH | " | $1.9 \times 10^{-5}$ | $6.2 \times 10^{-7}$ |
| 21 | GRGDFG-(p)Abz—GRGDF—OH | " | $3.5 \times 10^{-5}$ | $1.2 \times 10^{-6}$ |
| 22 | GRGDFG-(o)Abz—GRGDF—NH$_2$ | " | $9.3 \times 10^{-5}$ | $3.1 \times 10^{-6}$ |
| 23 | GRGDFG-(m)Abz—GRGDF—NH$_2$ | " | $5.2 \times 10^{-5}$ | $1.7 \times 10^{-6}$ |
| 24 | GRGDFG-(p)Abz—GRGDF—NH$_2$ | " | $5.9 \times 10^{-5}$ | $2.1 \times 10^{-6}$ |
| 25 | GRGDSG-(o)Abz—GRGDF—NH$_2$ | " | $6.3 \times 10^{-5}$ | $2.1 \times 10^{-6}$ |
| 26 | GRGDSG-(m)Abz—GRGDF—NH$_2$ | " | $9.1 \times 10^{-5}$ | $3.0 \times 10^{-6}$ |
| 27 | GRGDSG-(p)Abz—GRGDF—NH$_2$ | " | $5.2 \times 10^{-5}$ | $1.7 \times 10^{-6}$ |
| 28 | GRGDVG-(o)Abz—GRGDF—NH$_2$ | " | $9.2 \times 10^{-5}$ | $3.1 \times 10^{-6}$ |
| 29 | GRGDVG-(m)Abz—GRGDF—NH$_2$ | " | $4.6 \times 10^{-5}$ | $1.5 \times 10^{-6}$ |
| 30 | GRGDVG-(p)Abz—GRGDF—NH$_2$ | " | $2.6 \times 10^{-5}$ | $8.5 \times 10^{-7}$ |
| 31 | (BzRGDF)$_2$Dac—RGDF—OH | " | $7.4 \times 10^{-6}$ | $2.5 \times 10^{-7}$ |

Dab = 3,5-Diaminobenzoic acid residue, Abz = Aminobenzoic acid residue, Dac = 3,5-Diaminocyclohexanecarboxylic acid residue; Pht = Phthalic acid residue, Suc = Succinyl residue, Pda = Propanedicarboxylic acid residue, Bda = Butanedicarboxylic acid residue, Bz = Benzoyl, Hex = Hexanoyl.
*Estimated IC$_{50}$ adjusted to the values by the method of Plow et al. (vide supra).

EXAMPLE 1

(RGDFPG)$_2$Dab—G—OH

The synthesis with 0.1 mmol scale gave the TFA salt of peptide as a white solid (138 rag, 87 % yield). A portion (78 mg) of the product was purified on a μBondaPak C-18 column by using a gradient of 0% CH$_3$CN-0.1% TFA to 27% CH$_3$CN-0.1% TFA over a period of 30 rain and an isocratic of 27% CH$_3$CN-0.1% TFA over a period of 10 rain at a flow rate of 8 mL/min. The fractions containing the desired peptides were collected, lyophilized, dissolved in water, and salt-exchanged on a Sephadex column using a 20% acetic acid as the eluent. The elutes were lyophilized to give the pure peptide as the acetic acid salt (33.3 rag, white feather-like powder). Amino acid analysis: Asp 2.00, Gly 5.20, Arg 2.20, Pro 2.04, Phe 1,84. FAB-MS:1468.1 (M+i)+.

EXAMPLE 2

(RGDFPG)$_2$Dab—NH$_2$

The synthesis with 0.1 mmol scale gave the TFA salt of peptide as a white solid (141 rag, 91% yield). A portion (51 mg) of the product was purified on a μBondaPak C-18 column using a gradient of 0% CH$_3$CN-0.1% TFA to 27% CH$_3$CN-0.1% TFA over a period of 30 min and an isocratic of 27% CH$_3$CN-0.1% TFA in 10 min at a flow rate of 8 mL/min. The fractions containing the pure peptide were treated as described above for (GRGDFG)$_2$Dab-G-OH to give the pure peptide as the acetic acid salt (23.9 mg, white feather-like powder). Amino acid analysis: Asp 1.78, Gly 4.00, Arg 2.20, Pro 2.08, Phe 2.00. FAB-MS:1410.6 (M+1)+.

EXAMPLE 3

(RGDF)$_2$Lys—NH$_2$

The synthesis with 0.1 mmol scale gave the TFA salt of peptide as a white solid (162 rag, 100% yield). A portion (80 rag) of the .product was purified on a BondaPak C-18 column by using a gradient of 6% CH$_3$CN-0.1% TFA to 24% CH$_3$CN-0.1% TFA over a period of 30 rain at a flow rate of 7 mL/min. The fractions containing the pure peptide were treated as described above for (GRGDFG)$_2$Dab-G-OH to give the pure peptide as the acetic acid salt (43 mg, white feather-like powder). Amino acid analysis: Asp 1.98, Gly 2.00, Arg 2.20, Phe 1.98, Lys 0.90. FAB-MS:1097.3 (M+i)+.

EXAMPLE 4

(GRGDF)$_2$Lys—NH$_2$

The synthesis with 0.1 mmol scale gave the TFA salt of peptide as a white solid (182 mg, 100 % yield). A portion (80 mg) of the product was purified on a μBondaPak C-18 column by using a gradient of 0% CH$_3$CN-0.1% TFA to 40% CH$_3$CN-0.1% TFA over a period of 40 rain at a flow rate of 3 mL/min. The fractions containing the pure peptide were treated as described above for (GRGDFG)$_2$Dab-G-OH to give the pure peptide as the acetic acid salt (43 mg, white feather-like powder). Amino acid analysis: Asp 1.92, Gly 4.38, Arg 2.24, Phe 2.00, Lys 0.62. FAB-MS:1210.1 (M+1)+.

EXAMPLE 5

(GRGDF)$_2$Orn—NH$_2$

The synthesis with 0.1 mmol scale gave the TFA salt of peptide as a white solid (172 mg, 100 % yield). A portion (80 mg) of the product was purified on a μBondaPak C-18 column by using a gradient of 0% CH$_3$CN-0.1% TFA to 40% CH$_3$CN-0.1% TFA over a period of 40 rain at a flow rate of 3 mL/min. The fractions containing the pure peptide were treated as described above for (GRGDFG)$_2$Dab-G-OH to give the pure peptide as the acetic acid salt (52 mg, white feather-like powder). Amino acid analysis: Asp 1.88, Gly 4.38, Arg 2.26, Phe 2.00, Orn 0.78. FAB-MS:1197.2 (M+1)+.

EXAMPLE 6

(RGDF)$_2$Dac—NH$_2$

The synthesis with 0.1 mmol scale gave the TFA salt of the peptide as a white solid (80 mg, 70 % yield). A portion (20 mg) of the product was purified on a μBondaPak C-18 column by using a gradient of 10% CH$_3$CN-0.1% TFA to 60% CH$_3$CN-0.1% TFA over a period of 30 rain at a flow rate of 8 mL/min. The fractions containing the pure peptide were treated as described above for (GRGDFG)$_2$Dab-G-OH to give the pure peptide as the acetic acid salt (7 mg, white feather-like powder). Amino acid analysis: Asp 0.94, Gly 1.00, Arg 1.06, Phe 1.05. FAB-MS:1108.1 (M+1)+.

EXAMPLE 7

(BzRGDF)$_2$Lys—NH$_2$

The synthesis with 0.1 mmol scale gave the TFA salt of peptide as a white solid (80 rag, 62% yield). A portion of the product was purified on a μBondaPak C-18 column by using a gradient of 0% CH$_3$CN-0.1% TFA to 60% CH$_3$CN-0.1% TFA over a period of 40 rain at a flow rate of 7 mL/min. The fractions containing the pure peptide were treated as described above for (GRGDFG)$_2$Dab-G-OH to give the pure peptide as the acetic acid salt (17 mg, white feather-like powder). Amino acid analysis: Asp 1.98, Gly 2.08, Arg 2.00, Phe 2.04, Lys 0.92. FAB-MS:1293.1 (M+i)+.

EXAMPLE 8

(HexRGDF)$_2$Lys—NH$_2$

The synthesis with 0.1 mmol scale gave the TFA salt of peptide as a white solid (83 rag, 64% yield). A portion of the product was purified on a μBondaPak C-18 column by using a gradient of 0% CH$_3$CN-0.1% TFA to 60% CH$_3$CN-0.1% TFA over a period of 40 rain at a flow rate of 7 mL/min. The fractions containing the pure peptide were treated as described above for (GRGDFG)2Dab-G-OH to give the pure peptide as the acetic acid salt (16 mg, white feather-like powder). Amino acid analysis: Asp 1.96, Gly 2.07, Arg 2.10, Phe 2.00, Lys 0.92. FAB-MS: 1304.6 (M+1)+.

EXAMPLE 9

(BzRGDFP)$_2$Lys—NH$_2$

The synthesis with 0.1 mmol scale gave the TFA salt of peptide as a white solid (111 rag, 74% yield). A portion of the product was purified on a μBondaPak C-18 column by using a gradient of 0% CH$_3$CN-0.1% TFA to 60% CH$_3$CN-0.1% TFA over a period of 40 rain at a flow rate of 7 mL/min. The fractions containing the pure peptide were treated as described above for (GRGDFG)$_2$Dab-G-OH to give the pure peptide as the acetic acid salt (24 mg, white feather-like powder). Amino acid analysis: Asp 1.88, Gly 1.93, Arg 2.00, Pro 2.14, Phe 1.99, Lys 0.80. FAB-MS: 1499.2 (M+1)+.

EXAMPLE 10

(HexRGDFP)$_2$Lys—NH$_2$

The synthesis with 0.1 mmol scale gave the TFA salt of peptide as a white solid (123 rag, 83% yield). A portion of the product was purified on a μBondaPak C-18 column by using a gradient of 0% CH$_3$CN-0.1% TFA to 60% CH$_3$CN-0.1% TFA over a period of 40 rain at a flow rate of 7 mL/min. The fractions containing the pure peptide were treated as described above for (GRGDFG)$_2$Dab-G-OH to give the pure peptide as the acetic acid salt (36 mg, white feather-like powder). Amino acid Analysis: Asp 1.9, Pro 2.30, Phe 1.90, Lys 1.02. FAB-MS:1488.1 (M+1)+.

EXAMPLE 11

(p)Pht(RGDF—OH)$_2$

To the solution of TFA.R(Mtr)GDF-OH (40 rag, 0.048 mmol) in DMF (0.8 mL), diisopropylethylamine (45 mL) and the solution of terephthaloyl chloride (4.6 rag, 0.023 retool) in THF (0.5 mL) was added at 0 ° C. The reaction mixture was stirred for 1 hr at 0° C., then for 40 rain at room temperature. The reaction mixture was concentrated under vacuum to give oily residue. The residue was dissolved in a mixture of TFA (0.96 mL), thioanisol (46 μL), and EDT (5 μL), and stirred for 7 hr at room temperature. The solvent was removed by gentle stream of N$_2$ gas to give an oily residue which was precipitated by the addition of ether. The precipitate was washed with ether (3×15 mL) and purified on a SEPHADEX column (water). The peptide fractions were lyophilized to give a mixture of (p) Pht-RGDF-OH and (p)Pht(RGDF-OH)$_2$ as white feather-like powder. Two peptides were separated by HPLC: (p)Pht-RGDF-OH [3.5 mg, 23% yield, FABMS: 642.8 (M+1)+]; (p)Pht(RGDF-OH)$_2$ [9.6 rag, 37% yield, Amino acid analysis: Asp 0.94, Gly 1.00, Arg 1.05, Phe 1.00. FABMS:1117.1 (M+1)+].

EXAMPLE 12

Suc(RGDF—OH)$_2$

To the solution of TFA.R(Mtr)GDF-OH (40 rag, 0 048 mmol) in 0.7 N Na$_2$CO$_3$ ( 0.7 mL), the solution of succinyl chloride ( 3.7 mg, 0.024 mmol) in dioxane ( 0.2 mL) was added at 0 ° C. The reaction mixture was stirred for 1 hr at 0 ° C, then for 40 min at room temperature. The reaction mixture was lyophilized to give white solid. The solid was dissolved in the mixture of TFA (0.96 mL), thioanisol (46 μL), and EDT (5 μL), and stirred for 7 hr at room temperature. The solvent was removed by gentle stream of N$_2$ gas to give an oily residue which was precipitated by the addition of ether. The precipitate was washed with ether (3×15 mL) and purified on SEPHADEX column (water). The peptide fractions were lyophilized to give a mixture of SucRGDF-OH and Suc(RGDF-OH)$_2$ as white powder. Two peptides were separated by HPLC Suc-RGDF-OH [6.0 mg, 42% yield, FAB-MS: 594.6 (M+1)+]; Suc(RGDF-OH)$_2$[3.5 rag, 14% yield, Amino acid analysis: Asp 1.00, Gly 0.96, Arg 1.08, Phe 0.98. FAB-MS:1069.1 (M+1)+].

EXAMPLE 13

Pda (RGDF—OH)$_2$

This peptide was prepared as described above for Suc(RGDF-OH)$_2$ using glutaryl dichloride (4.1 mg, 0.024 mmol) to give two peptides as a white feather-like powder: Pda-RGDF-OH [4.9 rag, 34% yield, FAB-MS: 608.5 (M+1)+]; Pda(RGDF-OH)$_2$[11 mg, 42% yield, Amino acid analysis: Asp 0.91, Gly 1.05, Arg 1.06, Phe 1.00. FAB-MS:1083.3 (M+1)+].

EXAMPLE 14

Bda(RGDF—OH)$_2$

This peptide was prepared as described above for Suc(RGDF-OH)$_2$ using Adipoyl chloride (4.4 mg, 0.024 mmol) to give two peptides as white feather-like powder: Bda-RGDF-OH [8.9 rag, 60% yield, FAB-MS: 622.4 (M+1)+]; Bda(RGDF-OH)$_2$[18 mg, 68% yield, Amino acid analysis: Asp 0.90, Gly 1.01, Arg 1.04, Phe 1.00. FAB-MS: 1097.4 (M+1)+].

EXAMPLE 15

(GRGDFG)$_2$Dab—GRGDF—NH$_2$

The synthesis with 0.1 mmol scale gave the TFA salt of the peptide as a white solid (160 mg, 86% yield). A portion (25 mg) of the peptide was purified on a μBondapak C-18 column by using a gradient of 0% CH$_3$CN - 0.1% TFA to 66% CH$_3$CN - 0.1% TFA over a period of 50 min at a flow rate of 3 mL/min. The fractions containing the desired peptide were collected, lyophilized, dissolved in water, and salt-exchanged on a Sephadex column using 20% acetic acid as the eluent. The elutes were lyophilized to give the pure peptide as the acetic acid salt (10 mg, white feather-like powder). Amino acid analysis: Asp 3.00, Gly 7.83, Arg 3.15, Phe 2.82. FAB-MS:1863.4 (M+1)+.

EXAMPLE 16

(RGDF)$_2$Dac—RGDF—OH

The synthesis with 0.1 mmol scale gave the TFA salt of peptide as a white solid (148 mg, 91% yield). A portion (20 mg) of the product was purified on a μBondaPak C-18 column by using a gradient of 10% CH$_3$CN-0.1% TFA to 60% CH$_3$CN-0.1% TFA over a period of 30 rain at a flow rate of 8 mL/min. The fractions containing the pure peptide were treated as described above for (GRGDFG)$_2$Dab-GRGDF-NH$_2$ to give the pure peptide as the acetic acid salt (6 mg, white feather-like powder). Amino acid analysis: Asp 0.94, Gly 1.00, Arg 1.05, Phe 1.00. FAB-MS:1585.4 (M+1)+.

EXAMPLE 17

(GRGDF)$_2$Lys—GRGDF—NH$_2$

The synthesis with 0.1 mmol scale gave the TFA salt of the peptide as a white solid (221 mg, 100 % yield). A portion 30 (30 mg) of the product was purified on a μBondaPak C-18 column by using a gradient of 0% CH$_3$CN-0.1% TFA to 26% CH$_3$CN-0.1% TFA over a period of 40 rain at a flow rate of 3 mL/min. The fractions containing the pure peptide were treated as described above for (GRGDFG)$_2$Dab-GRGDF-NH$_2$ to give the pure peptide as the acetic acid salt (10 mg, white feather-like powder). Amino acid analysis: Asp 3.00, Gly 7.17, Arg 3.42, Phe 3.09, Lys 0.66. FAB-MS: 1743.7 (M+1)+.

EXAMPLE 18

(GRGDF)$_2$Orn—GRGDF—NH$_2$

The synthesis with 0.1 mmol scale gave the TFA salt of the peptide as a white solid (232 mg, 100 % yield). A portion (30 mg) of the product was purified on a μBondaPak C-18 column by using a gradient of 0% CH$_3$CN-0.1% TFA to 26% CH$_3$CN-0.1% TFA over a period of 40 rain at a flow rate of 3 mL/min. The fractions containing the pure peptide were treated as described above for (GRGDFG)$_2$Dab—GRGDF—NH$_2$ to give the pure peptide as the acetic acid salt (10 mg, white feather-like powder). Amino acid analysis: Asp 3.00, Gly 7.17, Arg 3.42, Phe 3.09, Lys 0.66. FAB-MS:1729.7 (M+1)+.

EXAMPLES 19

GRGDFG—(o)Abz—GRGDF—OH

The synthesis with 0.1 mmol scale gave the TFA salt of peptide as a white solid (105 rag, 80 % yield). The product contained two isolable isomers of the peptide. These isomers (38 mg) were separated on a μBondaPak C-18 column by using a gradient of 0% CH$_3$CN-0.1% TFA to 40% CH$_3$CN-0.1% TFA over a period of 40 rain at a flow rate of 3 mL/min. The fractions containing each of the pure peptides were treated as described above for (GRGDFG)$_2$Dab-GRGDF-NH$_2$ to give the acetic acid salt of pure peptides (17 mg, white feather-like powder). Amino acid analysis: Asp 2.91, Gly 6.69, Arg 3.36, Phe 3.00. FAB-MS:1259.8 (M+1)+.

EXAMPLE 20

GRGDFG—(m)Abz—GRGDF—OH

The synthesis with 0.1 mmol scale gave the TFA salt of peptide as a white solid (114 rag, 88 % yield). A portion (15 mg) of the product was separated on a μBondaPak C-18 column by using a gradient of 0% CH$_3$CN-0.1% TFA to 40% CH$_3$CN-0.1% TFA over a period of 40 min at a flow rate of 3 mL/min. The fractions containing the pure peptide were treated as described above for (GRGDFG)$_2$Dab-GRGDF-NH$_2$ to give the pure peptide as the acetic acid salt (10 mg, white feather-like powder). Amino acid analysis: Asp 2.00, Gly 4.82, Arg 2.30, Phe 2.04. FAB-MS:1259.3 (M+1)+.

EXAMPLE 21

GRGDFG—(p)Abz—GRGDF—OH

The synthesis with 0.1 mmol scale gave the TFA salt of peptide as a white solid (98 mg, 74 % yield). A portion (15 mg) of the product was purified on a μBondaPak C-18 column by using a gradient of 0% CH$_3$CN-0.1% TFA to 40% CH$_3$CN-0.1% TFA over a period of 40 rain at a flow rate of 3 mL/min. The fractions containing the pure peptide were treated as described above for (GRGDFG)$_2$Dab-GRGDF-NH$_2$ to give the pure peptide as the acetic acid salt (10 mg, white feather-like powder). Amino acid analysis: Asp 1.96, Gly 4.80, Arg 2.28, Phe 2.00. FABMS: 1259.3 (M+1)+.

EXAMPLE 2

GRGDFG—(o)Abz—GRGDF—NH$_2$

The synthesis with 0.1 mmol scale gave the TFA salt of peptide as a white solid (135 rag, 100 % yield). The product contained two isolable isomers of the peptide.

These isomers (30 rag) were separated on a μBondaPak C-18 column by using a gradient of 0% CH$_3$CN-0.1% TFA to 15% CH$_3$CN-0.1% TFA over a period of 30 rain at a flow rate of 10 mL/min. The fractions containing the each of the pure peptides were treated as described above for (GRGDFG)$_2$Dab-GRGDF-NH$_2$ to give the acetic acid salt of pure peptides (9 mg, white feather-like powder). Amino acid analysis: Asp 1.07, Gly 5.39, Arg 2.37, o-Abz 0.84, Phe 2.00. FAB-MS: 1258.3 (M+1)$^+$.

EXAMPLE 23

GRGDFG—(m)Abz—GRGDF—NH$_2$

The synthesis with 0.1 mmol scale gave the TFA salt of the peptide as a white solid (107 rag, 79 % yield). A portion (63 rag) of the product was purified on a μBondaPak C-18 column by using a gradient of 10% CH$_3$CN-0.1% TFA to 15% CH$_3$CN-0.1% TFA over a period of 30 rain at a flow rate of 10 mL/min. The fractions containing the pure peptide were treated as described above for (GRGDFG)$_2$Dab-GRGDF-NH$_2$ to give the pure peptide as the acetic acid salt (37 mg, white feather-like powder). Amino acid analysis: Asp 1.09, Gly 5.04, Arg 2.19, m-Abz 1.22, Phe 2.00. FAB-MS:1258.9 (M+1)$^+$.

EXAMPLE 24

GRGDFG—(p)Abz—GRGDF—NH$_2$

The synthesis with 0.1 mmol scale gave the TFA salt of the peptide as a white solid (114 rag, 84 % yield). A portion (41 mg) of the product was purified on a μBondaPak C-18 column by using a gradient of 10% CH$_3$CN-0.1% TFA to 15% CH$_3$CN-0.1% TFA over a period of 30 rain at a flow rate of 10 mL/min. The fractions containing the pure peptide were treated as described above for (GRGDFG)$_2$Dab-GRGDF-NH$_2$ to give the pure peptide as the acetic acid salt (35 mg, white feather-like powder). Amino acid analysis: Asp 1.40, Gly 5.13, Arg 2.59, p-Abz 1.98, Phe 2.00. FAB-MS: 1258.3 (M+1)$^+$.

EXAMPLES 25

GRGDSG—(o)Abz—GRGDF—NH$_2$

The synthesis with 0.1 mmol scale gave the TFA salt of the peptide as a white solid (118 rag, 86 % yield). The product contained two isolable isomers of the peptide. These isomers (45 rag) were separated on a μBondaPak C-18 column by using a gradient of 0% CH$_3$CN-0.1% TFA to 16% CH$_3$CN-0.1% TFA over a period of 30 min at a flow rate of 10 mL/min. The fractions containing the each pure peptides were treated as described above for (GRGDFG)$_2$Dab-GRGDF-NH$_2$ to give the acetic acid salt of pure peptides (11 mg, white feather-like powder). Amino acid analysis: Asp 1.85, Ser 1.01, Gly 4.55, Arg 2.17, o-Abz 0.58, Phe 1.00. FAB-MS: 1198.9 (M+1)$^+$.

EXAMPLE 26

GRGDSG—(m)Abz—GRGDF—NH$_2$

The synthesis with 0.1 mmol scale gave the TFA salt of the peptide as a white solid (134 rag, 97 % yield). A portion (62 mg) of the product was purified on a μBondaPak C-18 column by using a gradient of 10% CH$_3$CN-0.1% TFA to 16% CH$_3$CN-0.1% TFA over a period of 30 Bin at a flow rate of 10 mL/min. The fractions containing the pure peptide were treated as described above for (GRGDFG)$_2$Dab-GRGDF-NH$_2$ to give the pure peptide as the acetic acid salt (40 mg, white feather-like powder). Amino acid analysis: Asp 1.36, Ser 0.83, Gly 5.08, Arg 2.09, m-Abz 1.22, Phe 1.00. FAB-MS: 1198.5 (M+1)$^+$.

EXAMPLE 27

GRGDBG—(p)Abz—GRGDF—NH$_2$

The synthesis with 0.1 mmol scale gave the TFA salt of peptide as a white solid (137 mg, 100 % yield). A portion (61 mg) of the product was purified on a μBondaPak C-18 column by using a gradient of 10% CH$_3$CN-0.1% TFA to 16% CH$_3$CN-0.1% TFA over a period of 30 rain at a flow rate of 10 mL/min. The fractions containing the pure peptide were treated as described above for (GRGDFG)$_2$Dab-GRGDF-NH$_2$ to give the acetic acid salt of pure peptides (Isomer I, 16 mg, isomer II, 10 mg, white feather-like powder). Amino acid analysis: Asp 1.03, Set 0.84, Gly 5.02, Arg 2.02, p-Abz 1.64, Phe 1.00 FAB-MS: 1198.5 (M+1)$^+$.

EXAMPLE 28

GRGDVG—(o)Abz—GRGDF—NH$_2$

The synthesis with 0.1 mmol scale gave the TFA salt of the peptide as a white solid (139 mg, 100 % yield). The product contained two isolable isomers of the peptide. These isomers (49 mg) were separated on a μBondaPak C-18 column by using a gradient of 0% CH$_3$CN-0.1% TFA to 20% CH$_3$CN-0.1% TFA over a period of 30 rain at a flow rate of 10 mL/min. The fractions containing the each pure peptides were treated as described above for (GRGDFG)$_2$Dab-GRGDF-NH$_2$ to give the acetic acid salt of pure peptides (16 rag, white feather-like powder). Amino acid analysis: Asp 1.67, Gly 5.67, Arg 2.11, m-Abz 1.04, Val 1.00, Phe 1.00. FAB-MS:1211.2 (M+1)$^+$.

EXAMPLE 29

GRGDVG—(m)Abz—GRGDF—NH$_2$

The synthesis with 0.1 mmol scale gave the TFA salt of the peptide as a white solid (127 mg, 93 % yield). A portion (59 mg) of the product was purified on a μBondaPak C-18 column by using a gradient of 10% CH$_3$CN-0.1% TFA to 20% CH$_3$CN-0.1% TFA over a period of 30 rain at a flow rate of 10 mL/min. The fractions containing the pure peptide were treated as described above for (GRGDFG)$_2$Dab-GRGDF-NH$_2$ to give the pure peptide as the acetic acid salt (39 rag, white feather-like powder). Amino acid analysis: Asp 1.67, Gly 5.67, Arg 2.11, m-Abz 1.04, Val 1.00, Phe 1.00. FAB-MS: 1211.2 (M+1)$^+$.

EXAMPLE 30

GRGDVG—(p)Abz—GRGDF—NH$_2$

The synthesis with 0.1 mmol scale gave the TFA salt of the peptide as a white solid (126 mg, 91% yield). A portion (50 mg) of the product was purified on a μBondaPak C-18 column h by using a gradient of 10% CH$_3$CN-0.1% TFA to 20% CH$_3$CN-0.1% TFA over a period of 30 rain at a flow rate of 10 mL/min. The fractions containing the pure peptide were treated as described above for (GRGDFG)$_2$Dab-GRGDF-NH$_2$ to give the pure peptide as the acetic acid salt (27 mg, white feather-like powder). Amino acid analysis: Asp 1.81, Gly 5.27, Arg 1.96, p-Abz 1.19, Val 1.00, Phe 0.94. FAB-MS: 12 11.0 (M+1)+.

EXAMPLE 31

(BzRGDF)$_2$Dac—RGDF-OH

The synthesis with 0.05 mmol scale gave the TFA salt of peptide as a white solid (72 mg, 80% yield). A portion (10 rag) of the product was purified on a μBondaPak C-18 column by using a gradient of 0% CH$_3$CN-0.1% TFA to 55% CH$_3$CN-0.1% TFA over a period of 30 rain at a flow rate of 8 mL/min. The fractions containing the pure peptide were treated as described above for (GRGDFG)$_2$Dab-GRGDF-NH$_2$ to give the pure peptide as the acetic acid salt (3.0 mg, white feather-like powder). Amino acid analysis: Asp 1.00, Gly 0.95, Arg 1.01, Phe 0.93. FAB-MS:1793.4 (M+1)+.

Thus, while we have described what are presently the preferred embodiments of the present invention, other and further changes and modifications could be made without departing from the scope of the invention, and it is intended by the inventors to claim all such changes and modifications.

We claim:

1. A peptide selected from the group consisting of:
(RDGFPG)$_2$Dab—G—OH;
(RDGFPG)$_2$Dab—NH$_2$;
(RGDF)$_2$Lys—NH$_2$;
(GRGDF)$_2$Lys—NH$_2$;
(GRGDF)$_2$Orn—NH$_2$; and
(RGDF)$_2$Dac—NH$_2$.

2. A peptide selected from the group consisting of:
(BzRGDF)$_2$Lys—NH$_2$;
(HexRGDF)$_2$Lys—NH$_2$;
(BzRGDFP)$_2$Lys—NH$_2$; and
(HexRGDFP)$_2$Lys—NH$_2$.

3. A peptide selected from the group consisting of:
(p)Pht(RGDF—OH)$_2$;
Suc(RGDF—OH)$_2$;
Pda—(RGDF—OH)$_2$; and
Bda—(RGDF—OH)$_2$.

4. A peptide selected from the group consisting of:
(GRGDFG)$_2$Dab—GRGDF—NH$_2$;
(RGDF)$_2$Dac—RGDF—OH;
(GRGDSG)$_2$Dab—GRGDS—OH;
(GRGDF)$_2$Lys—GRGDF—NH$_2$;
(GRGDF)$_2$Orn—GRGDF—NH$_2$;
GRGDFG—(o)Abz—GRGDF—OH;
GRGDFG—(m)Abz—GRGDF—OH;
GRGDFG—(p)Abz—GRGDF—OH;
GRGDFG—(o)Abz—GRGDF—NH$_2$,
GRGDFG—(m)Abz—GRGDF—NH$_2$;
GRGDFG—(p)Abz—GRGDF—NH$_2$;
GRGDSG—(o)Abz—GRGDF—NH$_2$;
GRGDSG—(m)Abz—GRGDF—NH$_2$;
GFGDSG—(p)Abz—GRGDF—NH$_2$;
GRGDVG—(o)Abz—GRGDF—NH$_2$;
GRGDVG—(m)Abz—GRGDF—NH$_2$; and
GRGDVG—(p)Abz—GRGDF—NH$_2$.

5. A peptide having the formula:

(BzRGDF)$_2$Dac—RGDF—OH.

* * * * *

UNITED STATES PATENT AND TRADEMARK OFFICE
CERTIFICATE OF CORRECTION

PATENT NO. : 5,338,725     Page 1 of 6
DATED : August 16, 1994
INVENTOR(S) : Ojima et al.

It is certified that error appears in the above-indentified patent and that said Letters Patent is hereby corrected as shown below:

Replace "rag" with --mg-- in the following places:

Column 11, Line 40
    Column 11, Line 50
    Column 11, Line 58
    Column 12, Line 39
    Column 12, Line 40
    Column 13, Line 29
    Column 13, Line 44
    Column 13, Line 58
    Column 14, Line 6
    Column 14, Line 20
    Column 14, Line 22
    Column 14, Line 40
    Column 14, Line 47
    Column 14, Line 66
    Column 15, Line 8
    Column 15, Line 18
    Column 16, Line 21
    Column 16, Line 36
    Column 16, Line 66

UNITED STATES PATENT AND TRADEMARK OFFICE
CERTIFICATE OF CORRECTION

PATENT NO. : 5,338,725
DATED : August 16, 1994
INVENTOR(S) : Ojima et al.

It is certified that error appears in the above-indentified patent and that said Letters Patent is hereby corrected as shown below:

Replace "rag" with --mg-- in the following places:

Column 17, Line 1
    Column 17, Line 15
    Column 17, Line 16
    Column 17, Line 31
    Column 17, Line 46
    Column 17, Line 48
    Column 17, Line 62
    Column 18, Line 35
    Column 18, Line 51
    Column 19, Line 8

Replace "rain" with --min-- in the following places:

Column 8, Line 32
    Column 10, Line 31
    Column 10, Line 44
    Column 11, Line 44
    Column 11, Line 45
    Column 12, Line 43
    Column 12, Line 57
    Column 13, Line 4

UNITED STATES PATENT AND TRADEMARK OFFICE
CERTIFICATE OF CORRECTION

PATENT NO. : 5,338,725
DATED : August 16, 1994
INVENTOR(S) : Ojima et al.

It is certified that error appears in the above-indentified patent and that said Letters Patent is hereby corrected as shown below:

Replace "rain" with --min-- in the following places:

Column 13, Line 19
    Column 13, Line 32
    Column 13, Line 47
    Column 13, Line 61
    Column 14, Line 9
    Column 14, Line 26
    Column 15, Line 47
    Column 15, Line 61
    Column 16, Line 10
    Column 16, Line 25
    Column 17, Line 3
    Column 17, Line 19
    Column 17, Line 34
    Column 18, Line 15
    Column 18, Line 32
    Column 18, Line 48
    Column 18, Line 63
    Column 19, Line 11

UNITED STATES PATENT AND TRADEMARK OFFICE
CERTIFICATE OF CORRECTION

PATENT NO. : 5,338,725           Page 4 of 6
DATED : August 16, 1994
INVENTOR(S) : Ojima et al.

It is certified that error appears in the above-indentified patent and that said Letters Patent is hereby corrected as shown below:

| | |
|---|---|
| Column 8, Line 37 | now reads "Lumi Aggregometer 400rs", should read --Lumi Aggregometer 400VS --. |
| Column 10, Line 30 | now reads "(0.25 retool)", should read --(0.25 mmol)--. |
| Column 11, Table 1, | Example 16 now reads "(GRGDFG)", should read --(RGDF)--. |
| Column 11, Table 1, | Example 17 now reads "(GRGDFG)", should read --(GRGDF)--. |
| Column 11, Table 1 | Example 18 now reads "(GRGDFG)", should read --(GRGDF)--. |
| Column 11, Table 1 | Example 31 now reads " " ", should read --5--. |
| Column 11, Line 52 | now reads "(m+i)", should read --(m+1)--. |

UNITED STATES PATENT AND TRADEMARK OFFICE
CERTIFICATE OF CORRECTION

PATENT NO. : 5,338,725
DATED : August 16, 1994
INVENTOR(S) : Ojima et al.

It is certified that error appears in the above-indentified patent and that said Letters Patent is hereby corrected as shown below:

| | |
|---|---|
| Column 12, Line 40 | now reads "BondaPak", should read --$\mu$BondaPak--. |
| Column 12, Line 48 | now reads "m+i", should read --m+1--. |
| Column 14, Line 14 | now reads "Asp 1.9", should read --Asp 1.98--. |
| Column 14, Line 24 | now reads "0.023 retool", should read --0.023 mmol)--. |
| Column 14, Line 40 | now reads "(m+1)+]", should read --(m+1)$^+$]--. |
| Column 14, Line 48 | now reads "NA$^2$CO3", should read -- $NA_2CO_3$ --. |
| Column 14, Line 24 | now reads "0.023 retool", should read --0.023 mmol)--. |
| Column 14, Line 64 | now reads "(m+1)+]", should read --(m+1)$^+$]--. |
| Column 15, Line 58 | now reads "portion 30(30mg)", should read --portion (30mg)--. |
| Column 16, Line 63 | now reads "EXAMPLE 2", should read --EXAMPLE 22--. |

UNITED STATES PATENT AND TRADEMARK OFFICE
CERTIFICATE OF CORRECTION

PATENT NO. : 5,338,725
DATED : August 16, 1994
INVENTOR(S) : Ojima et al.

It is certified that error appears in the above-indentified patent and that said Letters Patent is hereby corrected as shown below:

| | |
|---|---|
| Column 17, Line 66 | now reads "30 Bin", should read --30 min--. |
| Column 18, Line 8 | now reads "GRGDBG", should read --GRGDSG--. |
| Column 18, Line 20 | now reads "Set 0.84", should read --Ser 0.84--. |
| Column 18, Line 61 | now reads "Column h by", should read --Column by--. |
| Column 19, Line 26 | now reads "(RDGFPG)"', should read --(RGDFPG)--. |
| Column 20, Line 24 | now reads "GFGDSG", should read --GRGDSG--. |
| Column 19, Line 27 | now reads "(RDGFPG).", should read --(RGDFPG)--. |

Signed and Sealed this

Twentieth Day of June, 1995

Attest:

BRUCE LEHMAN

*Attesting Officer*  *Commissioner of Patents and Trademarks*